(12) United States Patent
Jafari et al.

(10) Patent No.: US 8,434,479 B2
(45) Date of Patent: May 7, 2013

(54) FLOW RATE COMPENSATION FOR TRANSIENT THERMAL RESPONSE OF HOT-WIRE ANEMOMETERS

(75) Inventors: Mehdi M. Jafari, Laguna Hills, CA (US); Rhomere S. Jimenez, Winchester, CA (US); Edward R. McCoy, Vista, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 849 days.

(21) Appl. No.: 12/394,899

(22) Filed: Feb. 27, 2009

(65) Prior Publication Data

US 2010/0218765 A1    Sep. 2, 2010

(51) Int. Cl.
F16K 31/02  (2006.01)

(52) U.S. Cl.
USPC ............. 128/204.21; 128/204.18; 128/204.23

(58) Field of Classification Search ............. 128/204.18, 128/204.21–204.23
See application file for complete search history.

(56) References Cited

U.S. PATENT DOCUMENTS

| | | | |
|---|---|---|---|
| 269,929 | A | 1/1883 | Hanlon |
| 3,444,857 | A | 5/1969 | Godel |
| 3,481,333 | A | 12/1969 | Garrison |
| 3,485,243 | A | 12/1969 | Bird et al. |
| 3,688,794 | A | 9/1972 | Bird et al. |
| 4,141,354 | A | 2/1979 | Ismach |
| 4,211,221 | A | 7/1980 | Schwanbom et al. |
| 4,211,239 | A | 7/1980 | Raemer et al. |
| 4,241,756 | A | 12/1980 | Bennett et al. |
| 4,527,557 | A | 7/1985 | DeVries et al. |
| 4,592,349 | A | 6/1986 | Bird |
| 4,608,976 | A | 9/1986 | Suchy |
| 4,651,729 | A | 3/1987 | Rae |
| 4,699,137 | A | 10/1987 | Schroeder |
| RE32,553 | E | 12/1987 | Bennett et al. |
| 4,712,580 | A | 12/1987 | Gilman et al. |

(Continued)

FOREIGN PATENT DOCUMENTS

| | | |
|---|---|---|
| EP | 1228779 A1 | 8/2002 |
| WO | WO 2006/121372 | 11/2006 |
| WO | WO 2007/102866 | 9/2007 |

OTHER PUBLICATIONS

PCT International Search Report, Date of mailing: Jun. 23, 2010, International application No. PCT/US2010/025501, International filing date: Feb. 26, 2010, Applicant: Nellcor Puritan Bennett LLC.

(Continued)

Primary Examiner — Glenn Richman

(57) ABSTRACT

Systems and methods are described for application of a transitory corrective modification to a hot-wire anemometer flow voltage and/or calculated flow rate to compensate for transient thermal response of the anemometer during a change in mixture of a mixed gas being measured. According to one embodiment a method of applying the transitory corrective modification is provided. An output signal of an exhalation flow sensor of a medical ventilator is received. The flow sensor includes a hot-wire anemometer. The output signal is indicative of a rate of flow of expired gas by a patient. Transient thermal response of the hot-wire anemometer is compensated for by applying a corrective modification to the output signal or a value based thereon. The corrective modification is based at least in part on a fraction of inspired oxygen (FiO2) being supplied by the medical ventilator to the patient.

3 Claims, 5 Drawing Sheets

U.S. PATENT DOCUMENTS

| | | |
|---|---|---|
| 4,727,871 A | 3/1988 | Smargiassi et al. |
| 4,747,403 A | 5/1988 | Gluck et al. |
| 4,752,089 A | 6/1988 | Carter |
| 4,885,938 A | 12/1989 | Higashi |
| 4,889,116 A | 12/1989 | Taube |
| 4,921,642 A | 5/1990 | LaTorraca |
| 4,932,402 A * | 6/1990 | Snook et al. ............. 128/204.23 |
| 4,954,799 A | 9/1990 | Kumar |
| 4,957,107 A | 9/1990 | Sipin |
| 4,961,348 A | 10/1990 | Bonne |
| 4,991,576 A | 2/1991 | Henkin et al. |
| 4,993,269 A | 2/1991 | Guillaume et al. |
| 5,000,173 A | 3/1991 | Zalkin et al. |
| 5,007,420 A | 4/1991 | Bird |
| 5,020,516 A | 6/1991 | Biondi et al. |
| 5,020,532 A | 6/1991 | Mahoney et al. |
| 5,057,822 A | 10/1991 | Hoffman |
| 5,072,729 A | 12/1991 | DeVries |
| 5,072,737 A | 12/1991 | Goulding |
| 5,092,326 A | 3/1992 | Winn et al. |
| 5,109,838 A | 5/1992 | Elam |
| 5,116,088 A | 5/1992 | Bird |
| 5,127,400 A | 7/1992 | DeVries et al. |
| 5,134,995 A | 8/1992 | Gruenke et al. |
| 5,150,291 A | 9/1992 | Cummings et al. |
| 5,161,525 A | 11/1992 | Kimm et al. |
| 5,168,868 A | 12/1992 | Hicks |
| 5,178,155 A | 1/1993 | Mault |
| 5,237,523 A | 8/1993 | Bonne et al. |
| 5,237,987 A | 8/1993 | Anderson et al. |
| 5,255,675 A | 10/1993 | Kolobow |
| 5,259,373 A | 11/1993 | Gruenke et al. |
| 5,263,369 A | 11/1993 | Cutler |
| 5,269,293 A | 12/1993 | Loser et al. |
| 5,271,389 A | 12/1993 | Isaza et al. |
| 5,277,175 A | 1/1994 | Riggs et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,699 A | 4/1994 | Bonassa et al. |
| 5,309,901 A | 5/1994 | Beaussant |
| 5,319,540 A | 6/1994 | Isaza et al. |
| 5,325,861 A | 7/1994 | Goulding |
| 5,331,995 A | 7/1994 | Westfall et al. |
| 5,333,606 A | 8/1994 | Schneider et al. |
| 5,339,807 A | 8/1994 | Carter |
| 5,343,857 A | 9/1994 | Schneider et al. |
| 5,343,858 A | 9/1994 | Winefordner et al. |
| 5,351,522 A | 10/1994 | Lura |
| 5,357,946 A | 10/1994 | Kee et al. |
| 5,360,000 A | 11/1994 | Carter |
| 5,365,922 A | 11/1994 | Raemer |
| 5,368,019 A | 11/1994 | LaTorraca |
| 5,368,021 A | 11/1994 | Beard et al. |
| 5,377,671 A | 1/1995 | Biondi et al. |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,677 A | 3/1995 | Smith |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,437,272 A | 8/1995 | Fuhrman |
| 5,438,980 A | 8/1995 | Phillips |
| 5,443,075 A | 8/1995 | Holscher |
| 5,452,714 A | 9/1995 | Anderson et al. |
| 5,467,766 A | 11/1995 | Ansite et al. |
| 5,484,270 A | 1/1996 | Adahan |
| 5,494,028 A | 2/1996 | DeVries et al. |
| 5,497,767 A | 3/1996 | Olsson et al. |
| 5,503,140 A | 4/1996 | Winefordner et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,540,220 A | 7/1996 | Gropper et al. |
| 5,542,415 A | 8/1996 | Brady |
| 5,542,416 A | 8/1996 | Chalvignac |
| 5,544,674 A | 8/1996 | Kelly |
| 5,546,935 A | 8/1996 | Champeau |
| 5,549,106 A | 8/1996 | Gruenke et al. |
| 5,568,910 A | 10/1996 | Koehler et al. |
| 5,575,283 A | 11/1996 | Sjoestrand |
| 5,596,984 A | 1/1997 | O'Mahoney et al. |
| 5,606,968 A | 3/1997 | Mang |
| 5,617,847 A | 4/1997 | Howe |
| 5,630,411 A | 5/1997 | Holscher |
| 5,632,270 A | 5/1997 | O'Mahoney et al. |
| 5,645,048 A | 7/1997 | Brodsky et al. |
| 5,657,750 A | 8/1997 | Colman et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,664,563 A | 9/1997 | Schroeder et al. |
| 5,671,767 A | 9/1997 | Kelly |
| 5,672,041 A | 9/1997 | Ringdahl et al. |
| 5,673,689 A | 10/1997 | Power |
| 5,676,132 A | 10/1997 | Tillotson et al. |
| 5,678,537 A | 10/1997 | Bathe et al. |
| 5,683,232 A | 11/1997 | Adahan |
| 5,692,497 A | 12/1997 | Schnitzer et al. |
| 5,694,926 A | 12/1997 | DeVries et al. |
| 5,697,363 A | 12/1997 | Hart |
| 5,701,883 A | 12/1997 | Hete et al. |
| 5,701,889 A | 12/1997 | Danon |
| 5,705,735 A | 1/1998 | Acorn |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,614 A | 8/1998 | Gruenke et al. |
| 5,794,986 A | 8/1998 | Gansel et al. |
| 5,797,393 A | 8/1998 | Kohl |
| 5,803,064 A | 9/1998 | Phelps et al. |
| 5,813,399 A | 9/1998 | Isaza et al. |
| 5,823,179 A | 10/1998 | Grychowski et al. |
| 5,826,575 A | 10/1998 | Lall |
| 5,829,441 A | 11/1998 | Kidd et al. |
| 5,845,636 A | 12/1998 | Gruenke et al. |
| 5,857,458 A | 1/1999 | Tham et al. |
| 5,862,802 A | 1/1999 | Bird |
| 5,864,938 A | 2/1999 | Gansel et al. |
| 5,865,168 A | 2/1999 | Isaza |
| 5,868,133 A | 2/1999 | DeVries et al. |
| 5,875,783 A | 3/1999 | Kullik |
| 5,876,352 A | 3/1999 | Weismann |
| 5,881,717 A | 3/1999 | Isaza |
| 5,881,722 A | 3/1999 | DeVries et al. |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,925,831 A | 7/1999 | Storsved |
| 5,931,160 A | 8/1999 | Gilmore et al. |
| 5,934,274 A | 8/1999 | Merrick et al. |
| 5,937,856 A | 8/1999 | Jonasson et al. |
| 5,941,846 A | 8/1999 | Duffy et al. |
| 5,957,130 A | 9/1999 | Krahbichler et al. |
| 6,013,619 A | 1/2000 | Cochrane et al. |
| 6,024,089 A | 2/2000 | Wallace et al. |
| 6,041,777 A | 3/2000 | Faithfull et al. |
| 6,041,780 A | 3/2000 | Richard et al. |
| 6,047,860 A | 4/2000 | Sanders |
| 6,073,630 A | 6/2000 | Adahan |
| 6,076,523 A | 6/2000 | Jones et al. |
| 6,089,105 A | 7/2000 | Ricciardelli |
| 6,095,139 A | 8/2000 | Psaros |

| | | | | | | |
|---|---|---|---|---|---|---|
| 6,102,038 | A | 8/2000 | DeVries | 6,675,801 B2 | 1/2004 | Wallace et al. |
| 6,116,240 | A | 9/2000 | Merrick et al. | 6,718,974 B1 | 4/2004 | Moberg |
| 6,116,242 | A | 9/2000 | Frye et al. | 6,718,975 B2 | 4/2004 | Blomberg |
| 6,116,464 | A | 9/2000 | Sanders | 6,722,359 B2 | 4/2004 | Chalvignac |
| 6,119,686 | A | 9/2000 | Somerson et al. | 6,723,055 B2 | 4/2004 | Hoffman |
| 6,123,073 | A | 9/2000 | Schlawin et al. | 6,725,447 B1 | 4/2004 | Gilman et al. |
| 6,123,074 | A | 9/2000 | Hete et al. | 6,729,331 B2 | 5/2004 | Kay |
| 6,131,571 | A | 10/2000 | Lampotang et al. | 6,739,334 B2 | 5/2004 | Valeij |
| 6,135,106 | A | 10/2000 | Dirks et al. | 6,739,337 B2 | 5/2004 | Isaza |
| 6,135,967 | A | 10/2000 | Fiorenza et al. | 6,745,764 B2 | 6/2004 | Hickle |
| 6,142,150 | A | 11/2000 | O'Mahony | 6,761,165 B2 | 7/2004 | Strickland, Jr. |
| 6,148,814 | A | 11/2000 | Clemmer et al. | 6,761,167 B1 | 7/2004 | Nadjafizadeh et al. |
| 6,152,132 | A | 11/2000 | Psaros | 6,761,168 B1 | 7/2004 | Nadjafizadeh et al. |
| 6,152,135 | A | 11/2000 | DeVries et al. | 6,763,829 B2 | 7/2004 | Jaffe et al. |
| 6,158,432 | A | 12/2000 | Biondi et al. | 6,772,762 B2 | 8/2004 | Piesinger |
| 6,158,434 | A | 12/2000 | Lugtigheid et al. | 6,805,121 B1 | 10/2004 | Flood et al. |
| 6,161,539 | A | 12/2000 | Winter | 6,807,965 B1 | 10/2004 | Hickle |
| 6,176,234 | B1 | 1/2001 | Salter et al. | 6,814,074 B1 | 11/2004 | Nadjafizadeh et al. |
| 6,192,885 | B1 | 2/2001 | Jalde | 6,830,048 B2 | 12/2004 | Wruck et al. |
| 6,217,524 | B1 | 4/2001 | Orr et al. | 6,839,753 B2 | 1/2005 | Biondi et al. |
| 6,220,245 | B1 | 4/2001 | Takabayashi et al. | 6,866,040 B1 | 3/2005 | Bourdon |
| 6,269,812 | B1 | 8/2001 | Wallace et al. | 6,871,645 B2 | 3/2005 | Wartman et al. |
| 6,273,444 | B1 | 8/2001 | Power | 6,877,511 B2 | 4/2005 | DeVries et al. |
| 6,283,119 | B1 | 9/2001 | Bourdon | 6,886,558 B2 | 5/2005 | Tanaka |
| 6,287,264 | B1 | 9/2001 | Hoffman | 6,895,963 B1 | 5/2005 | Martin et al. |
| 6,295,330 | B1 | 9/2001 | Skog et al. | 6,896,713 B1 | 5/2005 | Eckerbom et al. |
| 6,295,985 | B1 | 10/2001 | Kock et al. | 6,938,619 B1 | 9/2005 | Hickle |
| 6,305,373 | B1 | 10/2001 | Wallace et al. | 6,960,854 B2 | 11/2005 | Nadjafizadeh et al. |
| 6,306,098 | B1 | 10/2001 | Orr et al. | 6,968,840 B2 | 11/2005 | Smith et al. |
| 6,308,553 | B1 | 10/2001 | Bonne et al. | 6,986,347 B2 | 1/2006 | Hickle |
| 6,308,706 | B1 | 10/2001 | Lammers et al. | 7,008,380 B1 | 3/2006 | Rees et al. |
| 6,309,360 | B1 | 10/2001 | Mault | 7,017,574 B2 | 3/2006 | Biondi et al. |
| 6,321,748 | B1 | 11/2001 | O'Mahoney | 7,032,589 B2 | 4/2006 | Kerechanin, II et al. |
| 6,325,785 | B1 | 12/2001 | Babkes et al. | 7,036,504 B2 | 5/2006 | Wallace et al. |
| 6,349,922 | B1 | 2/2002 | Rydin | 7,040,315 B1 | 5/2006 | Strömberg |
| 6,357,438 | B1 | 3/2002 | Hansen | 7,040,321 B2 | 5/2006 | Göbel |
| 6,358,215 | B1 | 3/2002 | Ricciardelli | 7,043,979 B2 | 5/2006 | Smith et al. |
| 6,360,745 | B1 | 3/2002 | Wallace et al. | 7,066,175 B2 | 6/2006 | Hamilton et al. |
| 6,369,838 | B1 | 4/2002 | Wallace et al. | 7,066,177 B2 | 6/2006 | Pittaway et al. |
| 6,371,113 | B1 | 4/2002 | Tobia et al. | 7,077,131 B2 | 7/2006 | Hansen |
| 6,390,988 | B1 * | 5/2002 | Robinson ............... 600/531 | RE39,225 E | 8/2006 | Isaza et al. |
| 6,412,483 | B1 | 7/2002 | Jones et al. | 7,117,438 B2 | 10/2006 | Wallace et al. |
| 6,415,788 | B1 | 7/2002 | Clawson et al. | 7,118,537 B2 | 10/2006 | Baddour |
| 6,419,634 | B1 | 7/2002 | Gaston, IV et al. | 7,121,277 B2 | 10/2006 | Ström |
| 6,439,229 | B1 | 8/2002 | Du et al. | 7,152,604 B2 | 12/2006 | Hickle et al. |
| 6,457,472 | B1 | 10/2002 | Schwartz et al. | 7,168,597 B1 | 1/2007 | Jones et al. |
| 6,463,930 | B2 | 10/2002 | Biondi et al. | 7,191,645 B2 | 3/2007 | Wible |
| 6,467,478 | B1 | 10/2002 | Merrick et al. | 7,195,013 B2 | 3/2007 | Lurie |
| 6,470,741 | B1 | 10/2002 | Fathollahzadeh | 7,210,478 B2 | 5/2007 | Banner et al. |
| 6,512,938 | B2 | 1/2003 | Claure et al. | 7,222,623 B2 | 5/2007 | DeVries et al. |
| 6,523,537 | B1 | 2/2003 | Mas Marfany | 7,229,430 B2 | 6/2007 | Hickle et al. |
| 6,523,538 | B1 | 2/2003 | Wikefeldt | 7,241,269 B2 | 7/2007 | McCawley et al. |
| 6,526,970 | B2 | 3/2003 | DeVries et al. | 7,270,126 B2 | 9/2007 | Wallace et al. |
| 6,533,730 | B2 | 3/2003 | Strom | 7,275,540 B2 | 10/2007 | Bolam et al. |
| 6,543,449 | B1 | 4/2003 | Woodring et al. | 7,291,115 B2 | 11/2007 | Cardona Burrul |
| 6,546,930 | B1 | 4/2003 | Emerson et al. | 7,302,949 B2 | 12/2007 | Pelerossi et al. |
| 6,550,479 | B1 | 4/2003 | Duxbury | 7,308,894 B2 | 12/2007 | Hickle |
| 6,553,991 | B1 | 4/2003 | Isaza | 7,316,231 B2 | 1/2008 | Hickle |
| 6,557,553 | B1 | 5/2003 | Borrello | 7,320,321 B2 | 1/2008 | Pranger et al. |
| 6,557,554 | B1 | 5/2003 | Sugiura | 7,334,578 B2 | 2/2008 | Biondi et al. |
| 6,564,798 | B1 | 5/2003 | Jalde | 7,337,778 B2 | 3/2008 | Martin et al. |
| 6,571,795 | B2 | 6/2003 | Bourdon | 7,347,825 B2 | 3/2008 | Vaughan et al. |
| 6,572,561 | B2 | 6/2003 | Mault | 7,369,757 B2 | 5/2008 | Farbarik |
| 6,575,164 | B1 | 6/2003 | Jaffe et al. | 7,370,650 B2 | 5/2008 | Nadjafizadeh et al. |
| 6,575,165 | B1 | 6/2003 | Cook et al. | 7,392,806 B2 | 7/2008 | Yuen et al. |
| 6,575,918 | B2 | 6/2003 | Kline | 7,428,902 B2 | 9/2008 | Du et al. |
| 6,584,973 | B1 | 7/2003 | Biondi et al. | 7,460,959 B2 | 12/2008 | Jafari |
| 6,606,994 | B1 | 8/2003 | Clark | 7,475,685 B2 | 1/2009 | Dietz et al. |
| 6,616,615 | B2 | 9/2003 | Mault | 7,484,508 B2 | 2/2009 | Younes |
| 6,619,289 | B1 | 9/2003 | Mashak | 7,487,773 B2 | 2/2009 | Li |
| 6,622,725 | B1 | 9/2003 | Fisher et al. | 7,487,778 B2 | 2/2009 | Freitag |
| 6,622,726 | B1 | 9/2003 | Du | 7,500,483 B2 | 3/2009 | Colman et al. |
| 6,629,934 | B2 | 10/2003 | Mault et al. | 7,509,957 B2 | 3/2009 | Duquette et al. |
| 6,631,716 | B1 | 10/2003 | Robinson et al. | 7,525,663 B2 | 4/2009 | Kwok et al. |
| 6,644,310 | B1 | 11/2003 | Delache et al. | 7,533,670 B1 | 5/2009 | Freitag et al. |
| 6,659,962 | B2 | 12/2003 | Ricciardelli | 7,547,285 B2 | 6/2009 | Kline |
| 6,668,824 | B1 | 12/2003 | Isaza et al. | 7,556,038 B2 | 7/2009 | Kirby et al. |
| 6,668,829 | B2 | 12/2003 | Biondi et al. | 7,556,042 B2 | 7/2009 | West et al. |
| 6,671,529 | B2 | 12/2003 | Claure et al. | 7,562,657 B2 | 7/2009 | Blanch et al. |

| | | |
|---|---|---|
| 7,565,905 B2 | 7/2009 | Hickle |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,654,802 B2 | 2/2010 | Crawford, Jr. et al. |
| 7,686,019 B2 | 3/2010 | Weiss |
| 7,694,677 B2 | 4/2010 | Tang |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| 7,740,591 B1 | 6/2010 | Starr et al. |
| 7,753,052 B2 | 7/2010 | Tanaka |
| 7,779,840 B2 | 8/2010 | Acker et al. |
| 7,784,461 B2 | 8/2010 | Figueiredo et al. |
| 7,810,497 B2 | 10/2010 | Pittman et al. |
| 7,814,906 B2 | 10/2010 | Moretti |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,855,716 B2 | 12/2010 | McCreary et al. |
| 7,861,716 B2 | 1/2011 | Borrello |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,891,354 B2 | 2/2011 | Farbarik |
| 7,893,560 B2 | 2/2011 | Carter |
| 7,900,626 B2 | 3/2011 | Daly |
| 7,913,690 B2 | 3/2011 | Fisher et al. |
| 7,984,714 B2 | 7/2011 | Hausmann et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| 8,181,648 B2 | 5/2012 | Perine et al. |
| 8,210,173 B2 | 7/2012 | Vandine |
| 8,210,174 B2 | 7/2012 | Farbarik |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0039833 A1 | 11/2001 | Engel et al. |
| 2002/0026941 A1 | 3/2002 | Biondi et al. |
| 2002/0112726 A1* | 8/2002 | Schmidt et al. ......... 128/204.23 |
| 2002/0138213 A1 | 9/2002 | Mault |
| 2003/0062045 A1 | 4/2003 | Woodring et al. |
| 2003/0106380 A1 | 6/2003 | Bonne et al. |
| 2003/0209242 A1 | 11/2003 | Hickle |
| 2003/0217747 A1 | 11/2003 | Hickle et al. |
| 2004/0138577 A1 | 7/2004 | Kline |
| 2004/0261793 A1 | 12/2004 | Stromberg et al. |
| 2005/0039748 A1 | 2/2005 | Andrieux |
| 2005/0070477 A1 | 3/2005 | Cochrane |
| 2005/0098177 A1 | 5/2005 | Haj-Yahya et al. |
| 2005/0112325 A1 | 5/2005 | Hickle |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0188083 A1 | 8/2005 | Biondi et al. |
| 2005/0217671 A1 | 10/2005 | Fisher et al. |
| 2005/0247311 A1 | 11/2005 | Vacchiano et al. |
| 2006/0032499 A1 | 2/2006 | Halsnes |
| 2006/0129054 A1 | 6/2006 | Orr et al. |
| 2006/0130839 A1 | 6/2006 | Bassovitch |
| 2006/0201507 A1 | 9/2006 | Breen |
| 2006/0249148 A1 | 11/2006 | Younes |
| 2006/0249153 A1 | 11/2006 | DeVries et al. |
| 2006/0286038 A1 | 12/2006 | Rairkar et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0062531 A1 | 3/2007 | Fisher et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0107728 A1 | 5/2007 | Ricciardelli et al. |
| 2007/0113854 A1 | 5/2007 | Mcauliffe |
| 2007/0125377 A1 | 6/2007 | Heinonen et al. |
| 2007/0142716 A1 | 6/2007 | Biondi |
| 2007/0144521 A1 | 6/2007 | DeVries et al. |
| 2007/0144523 A1 | 6/2007 | Bolam et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0227537 A1 | 10/2007 | Bemister et al. |
| 2007/0232952 A1 | 10/2007 | Baddour |
| 2007/0255160 A1 | 11/2007 | Daly |
| 2007/0284361 A1 | 12/2007 | Nadjafizadeh et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0119753 A1 | 5/2008 | Ricciardelli et al. |
| 2008/0135044 A1 | 6/2008 | Freitag et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman, Jr. |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241955 A1 | 10/2009 | Jafari et al. |
| 2009/0241964 A1 | 10/2009 | Aljuri et al. |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlmén et al. |
| 2009/0293877 A1 | 12/2009 | Blanch et al. |
| 2009/0299430 A1 | 12/2009 | Davies et al. |
| 2009/0301486 A1 | 12/2009 | Masic |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051029 A1 | 3/2010 | Jafari et al. |
| 2010/0059058 A1 | 3/2010 | Kuo |

| | | |
|---|---|---|
| 2010/0071689 A1 | 3/2010 | Thiessen |
| 2010/0071695 A1 | 3/2010 | Thiessen |
| 2010/0071696 A1 | 3/2010 | Jafari |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0241019 A1 | 9/2010 | Varga et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0282258 A1 | 11/2010 | Tailor et al. |
| 2010/0286544 A1 | 11/2010 | Tanaka et al. |
| 2010/0292601 A1 | 11/2010 | Dompeling et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0023879 A1 | 2/2011 | Vandine et al. |
| 2011/0041850 A1 | 2/2011 | Vandine et al. |
| 2011/0066060 A1 | 3/2011 | von Bahr et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |

OTHER PUBLICATIONS

"Understanding Hot-Wire Anemometry", Thermal Minutes, Qpedia, Advanced Thermal Solutions, Inc., 2007, pp. 13-17.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

"Understanding Hot-Wire Anemometry." Thermal Minutes. pp. 13-17.

Morris, S C, et al., "Transient Thermal Response of a Hot-Wire Anemometer." Institute of Physics Publishing. Meas. Sci. Technol. 14 (2003) 251-259.

Lundsgaard, J. S., et al. "Evaluation of a Constant-Temperature Hot-Wire Anemometer for Respiratory-Gas-Flow Measurements." Med. & Biol. Eng. & Comput., 1979, 17, 211-215.

Boone, U., et al. "Actuation-Based Microsensors." Institute of Physics Publishing. Smart Mater. Struct. 10 (2001) 1185-1195.

* cited by examiner

FLOW RATE COMPENSATION FOR TRANSIENT THERMAL RESPONSE OF HOT-WIRE ANEMOMETERS

BACKGROUND

1. Field

Embodiments of the present invention generally relate to flow sensors, and more particularly to systems and methods for compensating for transient thermal response of hot-wire anemometers resulting from a change in the mixture of gas being measured.

2. Description of the Related Art

Many medical ventilators use hot-wire anemometer flow sensors to measure flow rates both at the input (inspiratory) and output (expiratory) polls. Hot-wire anemometers are usually calibrated for specific gases and calibration parametric values are different depending on the gas type (e.g., air or oxygen). On the inspiratory side of a medical ventilator, anemometers with single gas calibration (e.g., air or oxygen) may be used in the appropriate gas conduits; however, at the expiratory side, the mixture of gas passing through an exhalation flow sensor varies based on breath phase and other factors.

Hot-wire anemometers operate with either constant current or constant temperature structure. They are customarily used as part of a Wheatstone bridge and electronic control circuits are used to maintain a fixed temperature across or current through the anemometer's filament. Changes in certain properties of the gas passing by the filament impact the heat exchange between the filament and the gas flow, thus leading to a change in the filament's temperature. Any deviation between the existing temperature and the reference temperature causes an imbalance in the bridge and the electronic control circuits respond by taking action to increase or decrease the current through the filament to adjust the temperature error. Notably, however, it takes some time (transient period) for the electronic temperature controller to respond and increase or decrease the filament current to adjust to the reference temperature. Thus, if a step change (mass flow rate) is generated in the composition of gas types in the mixture of gas passing through the exhalation flow sensor, a transient response (under or over estimation of the actual volumetric flow rate passing through the sensor) is observed.

In medical ventilators, accurate flow measurement is vital to the performance fidelity of pneumatic control systems, triggering and cycling event detection and reliable spirometry data. Thus, a real-time compensatory mechanism is needed to correct flow sensor measurements provided by hot-wire anemometer flow sensors during this transient period.

SUMMARY

Systems and methods are described for application of a transitory corrective modification to a hot-wire anemometer flow voltage and/or calculated flow rate to compensate for transient thermal response of the anemometer during a change in mixture of a mixed gas being measured. According to one embodiment, a method is provided for compensating for transient thermal response of a hot-wire anemometer. An output signal of an exhalation flow sensor including a hot-wire anemometer is received by one or more flow sensor processing modules of a medical ventilator. The output signal is indicative of a rate of flow of expired gas by a patient. In order to compensate for transient thermal response of the hot-wire anemometer, a corrective modification is applied to the output signal or a value based thereon by the one or more flow sensor processing modules. The corrective modification is based at least in part on a fraction of inspired oxygen (FiO2) being supplied to the patient by the medical ventilator. The one or more flow sensor processing modules are implemented in one or more microprocessors and one or more computer-readable media, which have instructions tangibly embodied therein that are executable by the one or more microprocessors.

In the aforementioned embodiment, the corrective modification may involve a constant and an exponentially decaying factor.

In various instances of the aforementioned embodiments, the corrective modification may be a function of a magnitude of a setting change of the FiO2, a magnitude of average flow rates through the flow sensor and dynamics of temperature control circuitry of the hot-wire anemometer.

In the context of various of the aforementioned embodiments, the corrective modification may involve multiplying the output signal or the value based thereon by a mix transition multiplier generally represented as:

$$M = 1.0 + K^* \Delta O2Conc^* e^{-t/T}$$

where,
K=0.00125
T=15 seconds
t=time elapsed since FiO2 setting change
$\Delta O2Conc$=Current FiO2 setting−Previous FiO2 setting.

In various instances of the aforementioned embodiments, an exhaled tidal volume may be determined based at least in part on the corrected output signal.

In the various instances of the aforementioned embodiments, a ventilatory cycle of the medical ventilator may be caused to transition from an expiratory phase to an inspiratory phase based at least in part on the corrected output signal.

Other embodiments of the present invention provide a medical ventilator, which includes a breathing gas delivery system, a flow sensor and a controller. The breathing gas delivery system has an inspiratory port through which breathing gas is delivered to a patient and an expiratory port through which expired gas is received from the patient. The flow sensor is operable to measure a rate of flow of expired gas and includes a hot-wire anemometer, operable to measure a rate of flow of expired gas. The controller is coupled to the breathing gas delivery system and the flow sensor and is operable to receive an output signal from the flow sensor indicative of the rate of flow of the expired gas. Responsive to of the output signal, the controller is further operable to compensate for transient thermal response of the hot-wire anemometer resulting from a change in concentration of gas types included within the expired gas by applying a corrective modification to the output signal or a value based thereon. The corrective modification is based at least in part on a fraction of inspired oxygen (FiO2) being supplied to the patient by the breathing gas delivery system.

In the aforementioned embodiment, the corrective modification may involve a constant and an exponentially decaying factor.

In various instances of the aforementioned embodiments, the corrective modification may be a function of a magnitude of a setting change of the FiO2, a magnitude of average flow rates through the flow sensor and dynamics of temperature control circuitry of the hot-wire anemometer.

In the context of various of the aforementioned embodiments, the corrective modification may involve multiplying the output signal or the value based thereon by a mix transition multiplier generally represented as:

$$M = 1.0 + K^* \Delta O2Conc^* e^{-t/T}$$

where,
K=0.00125
T=15 seconds
t=time elapsed since FiO2 setting change
ΔO2Conc=Current FiO2 setting Previous FiO2 setting.

In various instances of the aforementioned embodiments, an exhaled tidal volume may be determined based at least in part on the corrected output signal.

In the various instances of the aforementioned embodiments, a ventilatory cycle of the medical ventilator may be caused to transition from an expiratory phase to an inspiratory phase based at least in part on the corrected output signal.

Other embodiments of the present invention provide a program storage device readable by one or more microprocessors of a medical ventilator. The program storage device tangibly embodies a program of instructions executable by the one or more microprocessors to perform method steps for compensating for transient thermal response of a hot-wire anemometer resulting from a change in concentration of gas types being measured. According to the method steps an output signal of a flow sensor is received that is indicative of a rate of flow of expired gas by a patient. The flow sensor includes a hot-wire anemometer that is associated with an expiratory port of the medical ventilator. Transient thermal response of the hot-wire anemometer resulting from a change in concentration of gas types included within the expired gas is compensated for by applying a corrective modification to the output signal or a value based thereon that is based at least in part on a fraction of inspired oxygen (FiO2) being supplied to the patient by the medical ventilator.

In the aforementioned embodiment, the corrective modification may involve a constant and an exponentially decaying factor.

In various instances of the aforementioned embodiments, the corrective modification may be a function of a magnitude of a setting change of the FiO2, a magnitude of average flow rates through the flow sensor and dynamics of temperature control circuitry of the hot-wire anemometer.

In the context of various of the aforementioned embodiments, the corrective modification may involve multiplying the output signal or the value based thereon by a mix transition multiplier generally represented as:

$$M=1.0+K^*\Delta O2Conc^*e^{-t/T}$$

where,
K=0.00125
T=15 seconds
t=time elapsed since FiO2 setting change
ΔO2Conc=Current FiO2 setting−Previous FiO2 setting.

In various instances of the aforementioned embodiments, an exhaled tidal volume may be determined based at least in part on the corrected output signal.

In the various instances of the aforementioned embodiments, a ventilatory cycle of the medical ventilator may be caused to transition from an expiratory phase to an inspiratory phase based at least in part on the corrected output signal.

This summary provides only a general outline of some embodiments of the invention. Many other objects, features, advantages and other embodiments of the invention will become more fully apparent from the following detailed description, the appended claims and the accompanying drawings.

BRIEF DESCRIPTION OF THE DRAWINGS

A further understanding of the various embodiments of the present invention may be realized by reference to the figures which are described in remaining portions of the specification. In the figures, like reference numerals may be used throughout several of the figures to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION

Figure 1:
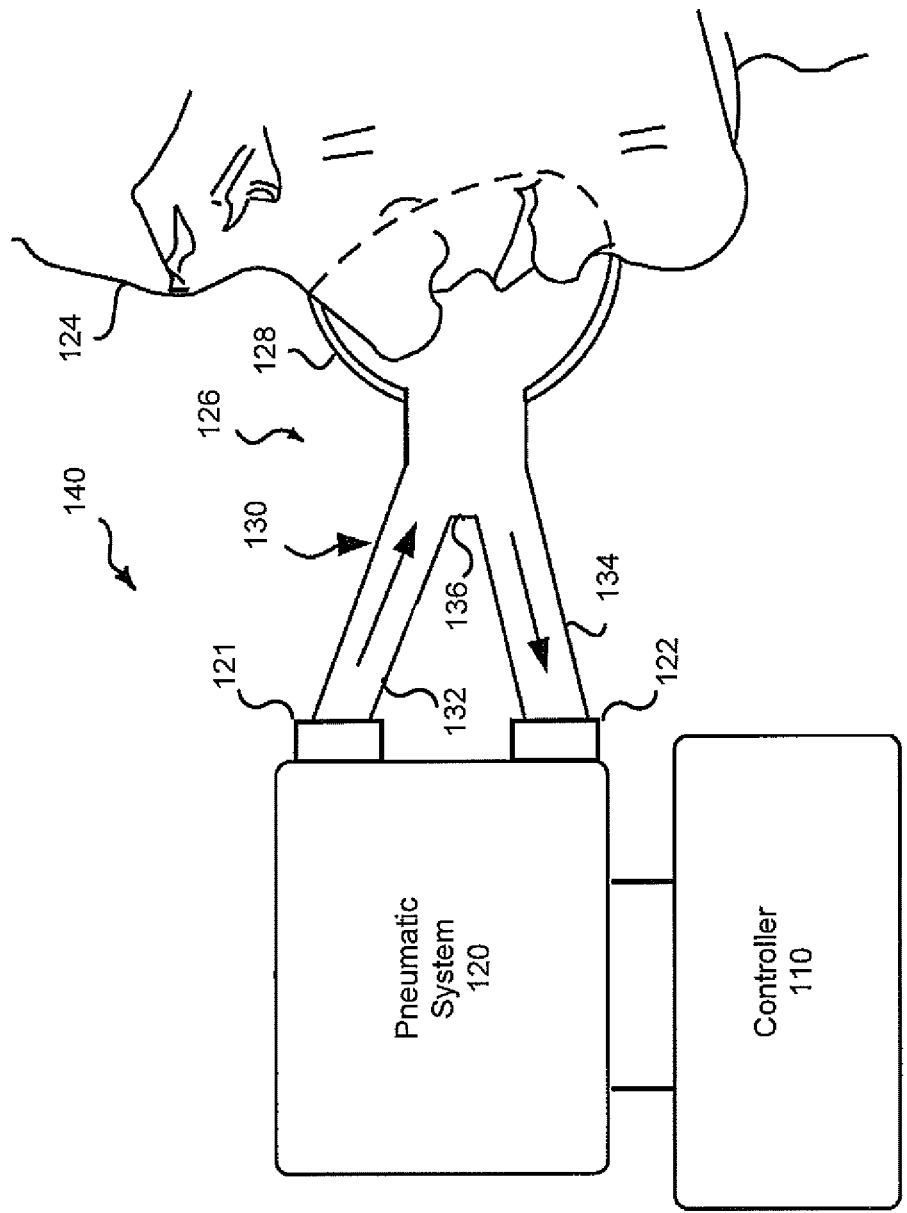
FIG. 1 depicts a simplified patient-ventilator block diagram in accordance with an embodiment of the present invention.

Systems and methods are described for application of a transitory corrective modification to a hot-wire anemometer flow voltage and/or calculated flow rate to compensate for transient thermal response of the anemometer during a change in mixture of a mixed gas being measured. Under steady state breathing gas conditions, approximation techniques to estimate the flow rate (and subsequently integrated volume) of exhaled gas passing through an exhalation hot-wire anemometer flow sensor are acceptable; however, it has been observed that upon a setting change in the desired fraction of inspired oxygen (FiO2), the reported exhaled tidal volumes demonstrate a transient behavior (i.e., increased reported volume for a setting decrease in desired oxygen concentration and decreased reported volume for a setting increase in desired oxygen concentration). This transient behavior lasts for a relatively short period of time (typically, less than 30 to 60 seconds) before the values stabilize to more accurate magnitudes. Embodiments of the present invention seek to compensate for this observed transient behavior by applying a transitory corrective modification to the anemometer's flow voltage and/or calculated flow rate during the transient period. According to one embodiment, the transitory corrective modification involves a constant and an exponentially decaying factor and is based on the magnitude of the desired FiO2 setting change, existing minute volume (magnitude of the average flow rates through the sensor) and the anemometer characteristics (e.g., dynamics of the temperature control circuitry).

In the following description, for the purposes of explanation, numerous specific details are set forth in order to provide a thorough understanding of embodiments of the present invention. It will be apparent, however, to one skilled in the art that embodiments of the present invention may be practiced without some of these specific details and/or other embodiments may incorporate other details as necessary to realize the design concept and goals in specific platforms with specific characteristics.

Embodiments of the present invention may include various steps, which will be described below. The steps may be performed by hardware components or may be embodied in machine-executable instructions, such as firmware or software, which may be used to cause a general-purpose or special-purpose processor programmed with the instructions to perform the steps. Alternatively, the steps may be performed and/or facilitated by a combination of hardware, software, firmware and/or one or more human operators, such as a clinician.

Embodiments of the present invention may be provided as a computer program product which may include a machine-readable medium having stored thereon instructions which may be used to program a processor associated with a ventilation control system to perform various processing. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, MultiMedia Cards (MMCs), secure digital (SD) cards, such as miniSD and microSD cards, or other type of media/machine-readable medium suitable for storing electronic instructions. Moreover, embodiments of the present invention may also be downloaded as a computer program product. The computer program may be transferred from a remote computer to a requesting computer by way of data signals embodied in a carrier wave or other propagation medium via a communication link (e.g., a modem or network connection). For example, various subsets of the functionality described herein may be provided within a legacy or upgradable ventilation system as a result of installation of a software option or performance of a firmware upgrade.

As used herein, the terms "connected" or "coupled" and related terms are used in an operational sense and are not necessarily limited to a direct physical connection or coupling. Thus, for example, two devices of functional units may be coupled directly, or via one or more intermediary media or devices. As another example, devices or functional units may be coupled in such a way that information can be passed there between, while not sharing any physical connection one with another. Based on the disclosure provided herein, one of ordinary skill in the art will appreciate a variety of ways in which connection or coupling exists in accordance with the aforementioned definition.

As used herein, the phrases "in one embodiment," "according to one embodiment," and the like generally mean the particular feature, structure, or characteristic following the phrase is included in at least one embodiment of the present invention, and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic.

FIG. 1 depicts a simplified patient-ventilator block diagram in accordance with an embodiment of the present invention. An exemplary ventilator in which embodiments of the present invention may be utilized is the Puritan Bennett® 840™ Ventilator System (available from Nellcor Puritan Bennett LLC of Boulder, Colo.), which can be upgraded and customized with various software options to meet changing clinical needs.

In the current example, a ventilator 140 includes a pneumatic system 120 and a controller 110. The pneumatic system 120 circulates breathing gases to and from patient 124 via an airway 126, which couples the patient 124 to the pneumatic system 120 via physical patient interface 128 and a breathing circuit 130. In the current example, breathing circuit 130 is a two-limb circuit, which carries breathing gas to the patient 124 through an inspiratory port 121 of the ventilator 140 and carries exhaled gas from the patient 124 through an expiratory port 122 of the ventilator 140. A wye fitting 136 may be provided as shown to couple the patient interface 128 to the breathing circuit 130. In alternative embodiments, the breathing circuit 130 may be a one-limb circuit.

While the present example, is discussed in the context of a non-invasive setting, such as with the use of a facial breathing mask, embodiments of the present invention are applicable in a variety of settings, and the present description contemplates that the patient interface 128 may be invasive or non-invasive, and of any configuration suitable for communicating breathing gas to and expired gas from an airway of the patient 128. Examples of other patient interface devices include nasal masks, nasal/oral masks, nasal prongs, full-face masks, tracheal tubes, endotracheal tubes, nasal pillows, etc.

Pneumatic system 120 may be configured in a variety of ways. For example, it may include inspiratory and expiratory modules (not shown) coupled with an inspiratory limb 132 and an expiratory limb 134, respectively, of the breathing circuit 130. A compressor (not shown) may provide a gas source for ventilatory support via inspiratory limb 132. The pneumatic system 120 may include a variety of other components, including sources for pressurized air and/or oxygen, mixing modules, valves, sensors, tubing, accumulators, filters, etc.

While the present example is discussed in the context of a medical ventilator 140 having a particular breathing gas delivery system, i.e., pneumatic system 120, embodiments of the present invention are applicable in a variety of settings, and the present description contemplates other breathing gas delivery systems, including, but not limited to piston based systems, turbopump based systems and the like.

As will be described in detail below, the various ventilator system and method embodiments described herein may be provided with compensation mechanisms that provide flow rate compensation to address observed transient thermal response of hot-wire anemometer flow sensors, such as an exhalation flow sensor (not shown) positioned at or near the expiratory port 122, resulting from a change in the composition of gas being measured. As indicated above, the mixture of gas passing through an exhalation flow sensor varies depending on breath phase and operator-set desired FiO2. Various compensation mechanisms described herein perform real-time correction without requiring re-calibration of the flow sensor and without requiring advanced knowledge, measurement or analysis of the gas composition of the expired gas being measured. Rather, embodiments of the present invention allow fast and accurate correction of flow sensor output data relating to patient expiration based on a known transfer function of the flow sensor and the magnitude of change of FiO2. The present discussion will focus on specific exemplary embodiments, though it should be appreciated that the present systems and methods are applicable to a wide variety of ventilator devices and configurations.

Figure 2:
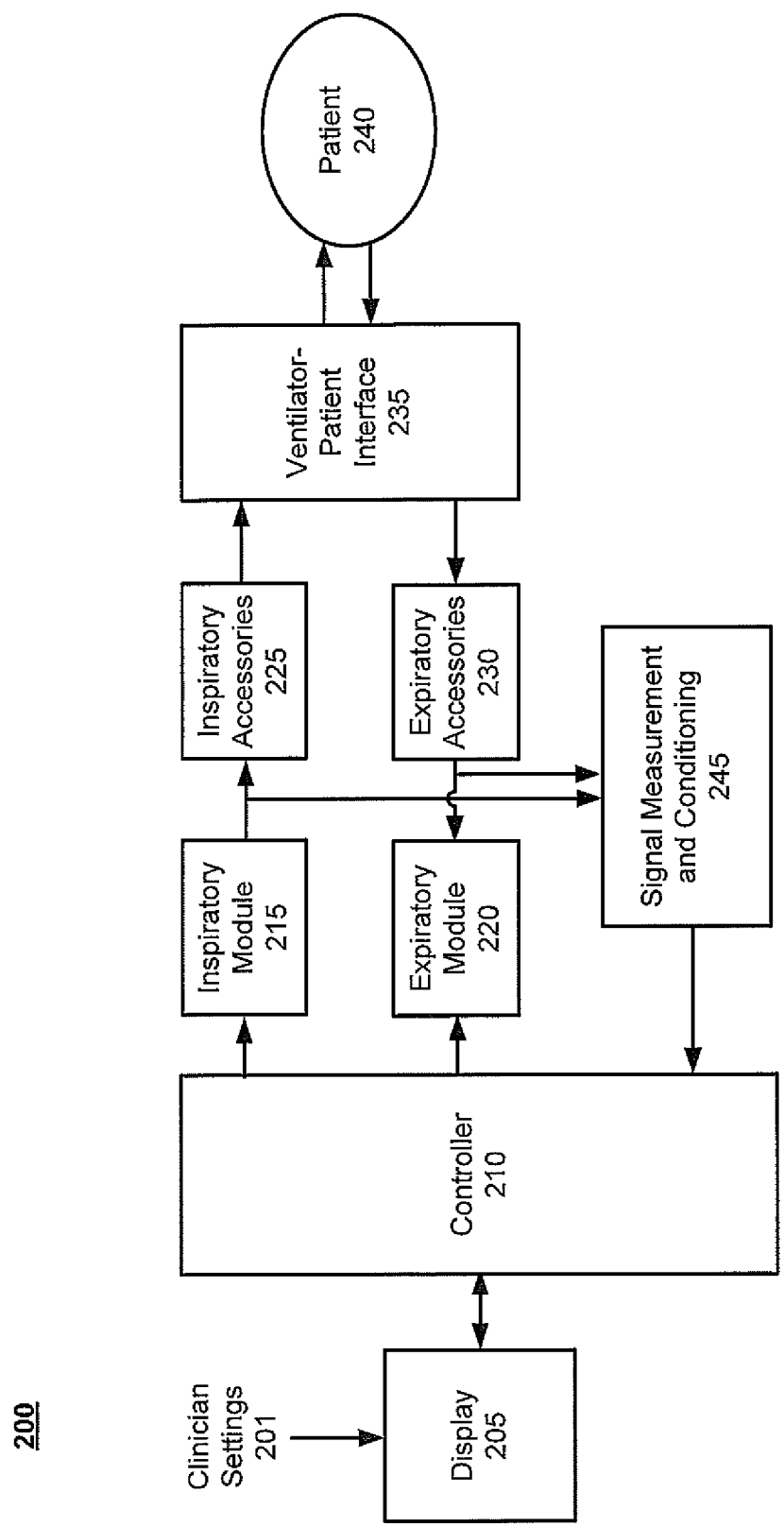
FIG. 2 depicts a more detailed, but still simplified patient-ventilator modular block diagram in accordance with one or more embodiments of the present invention.

FIG. 2 depicts a more detailed, but still simplified patient-ventilator modular block diagram in accordance with one or more embodiments of the present invention. In the current example, the major functional units/components of a patient-ventilator system 200 are illustrated, including an inspiratory module 215, an expiratory module 220, inspiratory accessories 225, expiratory accessories 230, a ventilator-patient interface 235, a signal measurement and conditioning module 245, a controller 210, a display 205 and a patient 240.

Inspiratory module 215 may include a gas source, regulators and various valving components. The expiratory module 220 typically includes an exhalation valve and a heated filter. The inspiratory accessories 225 and the expiratory accessories 230 typically include gas delivery/exhaust circuits and other elements, such as filters, humidifiers and water traps.

Depending upon the particular type of ventilation (e.g., invasive ventilation or noninvasive ventilation), the ventilator-patient interface 235 may include endotracheal tubes or masks or others as appropriate for invasive or noninvasive use as applicable.

Signal measurement and conditioning module 245 receives raw measurement data from various sensors that may be part of the patient-ventilator system, including, but not limited to physiological sensors, pressure sensors, hot-wire anemometer flow sensors and the like. The signal measurement and conditioning module 245 may then manipulate various analog signals in such a way that they meet the requirements of the next stage for further processing. According to one embodiment, the signal measurement and conditioning module 245 may transform the raw sensor measurements into data in a form useable by controller 210. For example, pressure and flow sensor data may be digitized and/or flow sensor data may be integrated to compute volume measurements.

As discussed earlier, gas delivered to patient 240 and/or expiratory gas flow returning from patient 240 to the ventilation system may be measured by one or more flow sensors (not shown). According to embodiments of the present invention, the expiratory flow sensor is a hot-wire anemometer flow sensor.

As described further below, according to one embodiment, during exhalation, controller 210 receives an output signal of an exhalation flow sensor and applies a corrective modification to the output signal based on a change in magnitude (if any) between a current FiO2 setting and a previous FiO2 setting. Controller 210 may use the corrected output signal in connection with downstream processing, including, but not limited to determining an exhaled tidal volume and transitioning a ventilatory cycle of the medical ventilator from an expiratory phase to an inspiratory phase. During inhalation, controller 210 commands actuators in the inspiratory module 215 to regulate gas delivery (e.g., flow, volume and/or oxygen mix) through the ventilator-patient interface 235 responsive to parameter values of a respiratory predictive model.

Controller 210 is also operatively coupled with an operator interface (e.g., display 205), which allows an operator, such as a clinician, to interact with the ventilator (e.g., change ventilator settings, select operational modes, view monitored parameters, etc.). In one embodiment, display 205 is touch-sensitive, enabling it to serve both as an output device and an input device for purposes of receiving clinician settings 201.

In one embodiment, the functionality of one or more of the above-referenced functional units may be merged and/or distributed in various combinations. For example, controller 210 and signal measurement and conditioning module 245 may be combined. Controller 210 may also be broken into multiple functional units, including, an inspiratory path controller, an expiratory path controller, for example. Moreover, the various functional units can be communicatively coupled using any suitable communication method (e.g., message passing, parameter passing, and/or signals through one or more communication paths, etc.). Additionally, the functional units can be physically connected according to any suitable interconnection architecture (e.g., fully connected, hypercube, etc.).

According to embodiments of the invention, the functional units can be any suitable type of logic (e.g., digital logic, software code and the like) or combination thereof for executing the operations described herein. Any of the functional units used in conjunction with embodiments of the invention can include machine-readable media including instructions for performing operations described herein. Machine-readable media include any mechanism that tangibly embodies information in a form readable by a machine (e.g., one or more microprocessors of a medical ventilator). For example, a machine-readable medium includes, but is not limited to, read only memory (ROM), random access memory (RAM), magnetic disk storage media, optical storage media or Rash memory devices.

Figure 3:
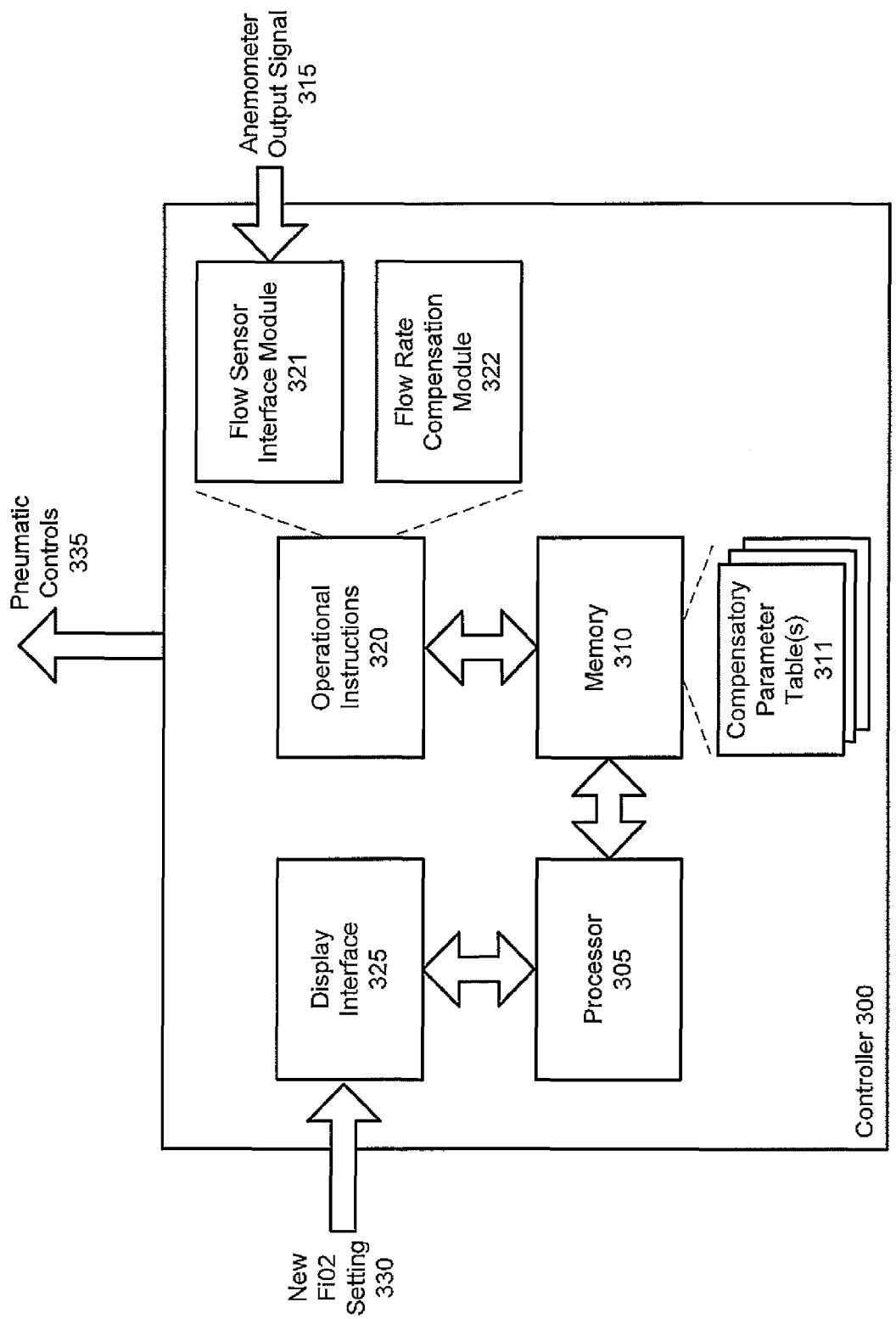
FIG. 3 depicts a modular block diagram of a controller in accordance with an embodiment of the present invention.

FIG. 3 depicts a modular block diagram of a controller 300 in accordance with an embodiment of the present invention. According to the present example, controller 300 includes memory 310, operational instructions 320 tangibly embodied within memory 310, one or more processors 305 and a display interface 325. Controller 300 receives clinician settings, including a new desired FiO2 setting 330, flow sensor readings, such as anemometer output signal 315 and issues commands, such as pneumatic controls 335, to a breathing gas delivery system (e.g., pneumatic system 120) in order to control the breathing assistance provided to the patient by the ventilator. The specific commands may be based on inputs received from patient 128, pneumatic system 128, sensors, display interface 325 and/or other components of the ventilator.

Processor(s) 305 may be any processor(s) known in the art that are capable of executing the various operational instructions 320 maintained in memory 310, issuing pneumatic controls 335 and otherwise interacting with various other functional units of the ventilator system, such as display 205 via the display interface 325. In one embodiment of the present invention, processor(s) 305 may receive interrupts on a periodic basis to trigger flow rate compensation processing, ventilator configuration and/or control processing activities. Such interrupts may be generated by a timer. Alternatively, the interrupts may be responsive to availability of sensor measurements, e.g., anemometer output signal 315, and/or operator input, e.g., new FiO2 setting 330. Such interrupts may be received using any interrupt scheme known in the art including, but not limited to, using a polling scheme where processor(s) 305 periodically review an interrupt register, or using an asynchronous interrupt port of processor(s) 305. Alternatively or additionally, the processor(s) 305 may proactively request sensor measurements, such as anemometer output signal 315, be provided from the signal measurement and conditioning module 245 and/or operator input be provided on a periodic or as needed basis. Based on the disclosure provided herein, one of ordinary skill in the art will recognize a variety of interrupt and/or polling mechanisms that may be used in relation to different embodiments of the present invention.

Memory 310 includes operational instructions 320 that may be software instructions, firmware instructions or some combination thereof. Operational instructions 320 are executable by processor(s) 305, and may be used to cause processor(s) 305 to receive anemometer output signal 315, correct the flow voltage and/or calculated flow rate to compensate for the observed transient thermal response during a change in mixture of breathing gas (e.g., increase or decrease in FiO2) and to deliver commands, such as pneumatic controls 335, to the breathing gas delivery system (e.g., pneumatic system 120).

In one embodiment of the present invention, processor(s) 305 apply a corrective modification to anemometer output signal 315 by executing one or more flow sensor processing modules that are part of operational instructions 320, e.g., flow sensor interface module 321 and flow rate compensation module 322. Flow sensor interface module 321 may represent a sensor-specific interface or protocol for receiving and interpreting measurement data from an exhalation flow sensor. Exemplary flow sensors that may be used as the exhalation flow sensor include hot-wire mass flow sensors available from TSI Incorporated of Shoreview, Minn.

Flow rate compensation module 322 may represent a sensor-specific module for correcting sensor measurement data received from the exhalation flow sensor. According to one embodiment, the corrective modification is in the form of a mix transition multiplier, M, to be applied to the anemometer output signal 315. During the transition period, e.g., within 30 to 60 seconds of enablement of the new FiO2 setting 330, the goal of applying the multiplier is to correct for the transient behavior of the hot-wire anemometer flow sensor. During non-transition periods, the goal of the multiplier is to leave the anemometer output signal 315 unchanged.

In one embodiment, flow rate compensation module 322 may be generalized by expressing the corrective modification as a parameterized equation having a constant and an exponentially decaying factor (see, e.g., EQ #1, below), the compensatory parameters of which (e.g., K and T) may be stored in one or more compensatory parameter table(s) 311 and indexed or otherwise retrieved based on one or more of flow sensor type, manufacturer, models, etc. These parameters may have tabulated default values as well as updated values determined in accordance with calibration procedures executed by the ventilator (e.g., as part of ventilator Self Test process). According to one embodiment, updated values may capture any variations caused by aging or other effects over time.

$$M = 1.0 + K^* \Delta O2Conc^* e^{-t/T} \quad \text{(EQ \#1)}$$

where,
K=0.00125
T=15 seconds
t=time elapsed since FiO2 setting change
ΔO2Conc=New FiO2 setting−Previous FiO2 setting It is contemplated that the transient period will likely vary from manufacturer to manufacturer and even among flow sensor products distributed by the same manufacturer. Consequently, the transient period or a factor based thereon (e.g., T in EQ #1) may be a configurable parameter retrieved from memory (e.g., from one or more compensatory parameter table(s) 311 provisioned by the medical ventilator manufacturer, for example, prior to shipment, provided with installation software shipped with the medical ventilator or available online) during start-up or self-test processing of a medical ventilator. Based on the disclosure provided herein, one of ordinary skill in the art will appreciate a variety of ways of obtaining information regarding the transient period for different hot-wire anemometer flow sensors. For example, such data can be obtained empirically in a test bench setting or such information can be obtained from data sheets or other specifications provided by manufacturers of the hot-wire anemometer flow sensors. According to one embodiment, compensatory parameters (e.g., K and T of EQ #1) are based in part on existing minute volume (magnitude of the average flow rates through the sensor) and anemometer characteristics (e.g., dynamics of the temperature control circuitry). Faster or slower flow of gas (higher or lower minute volume) and faster or slower response time of the sensor's control circuit would impact the transient time. Therefore, either empirically or as a part of a calibration process, K and T values may be determined and saved for an applicable range of minute volumes using appropriate resolution steps for each specific sensor.

As indicated earlier, a change in composition of breathing gas being supplied to a patient, results in a change in the composition of exhalation gas being measured by the exhalation flow sensor. The observed transient response of hot-wire anemometer flow sensors causes under or over estimation of the actual volumetric flow rate passing through the sensor when the FiO2 setting is increased or decreased, respectively. Thus, in EQ #1, when the FiO2 setting change reflects an increase in oxygen concentration the mix transition multiplier has an additive effect (multiplier greater than one) on the value to which it is applied and when the FiO2 setting change reflects a decrease in oxygen concentration, the mix transition multiplier has a subtractive effect (multiplier less than one) on the value to which it is applied.

According to embodiments of the present invention, each time anemometer output signal 315 is received by flow sensor interface module 321, it is corrected, if needed, by applying a mix transition multiplier (e.g., M of EQ #1). Alternatively, application of the corrective modification can be performed during downstream calculations involving use of the anemometer output signal 315. Table lookup mechanisms may also be employed in which corrected values are stored in one or more lookup tables. In yet other alternative embodiments, rather than applying a mix transition multiplier (e.g., M of EQ #1) to every anemometer output signal 315 or subsequent value based thereon, the corrective modification may be applied only during the transient period—leaving anemometer output signals 315 generated outside of the transient period unchanged.

Figure 4:
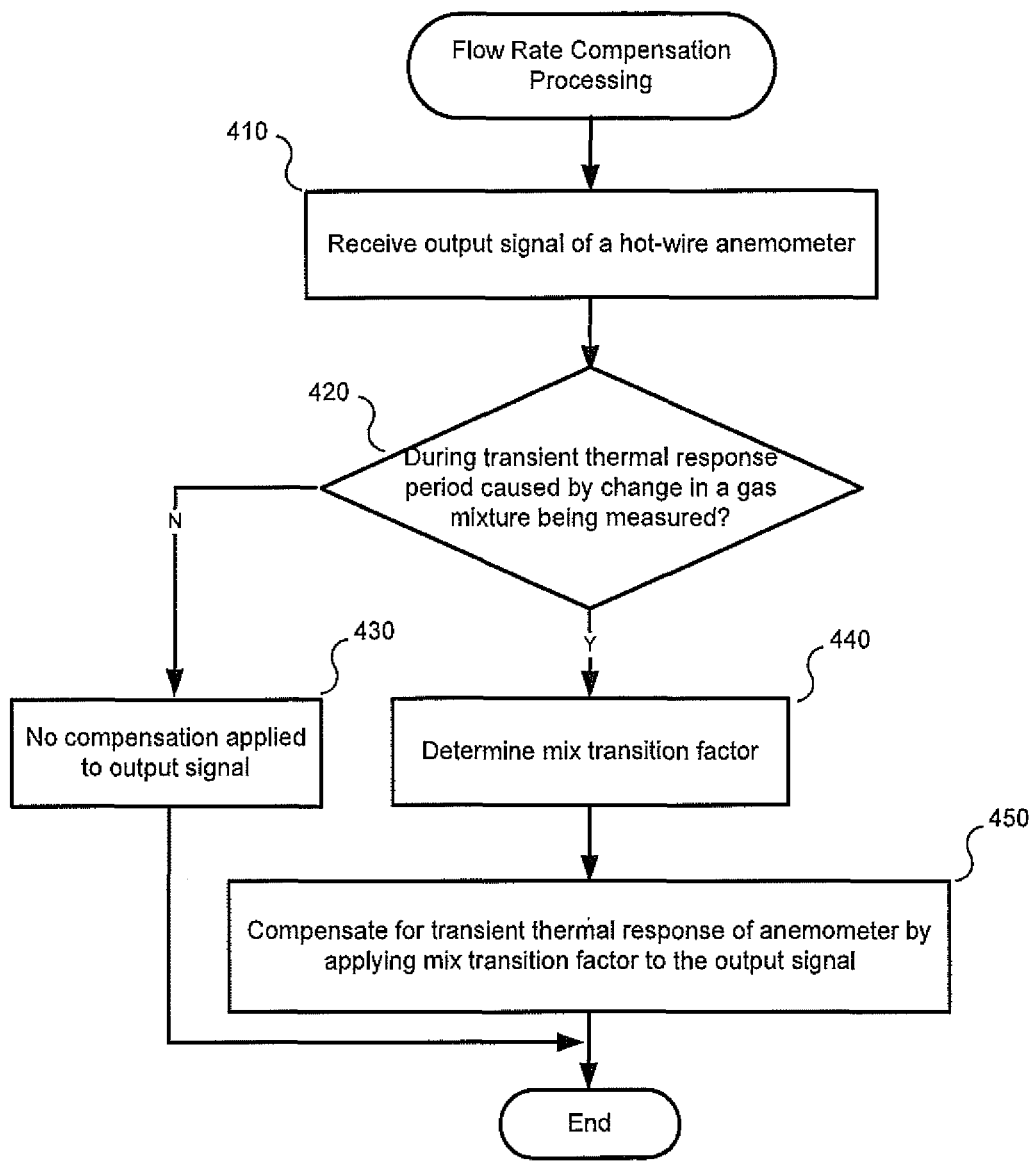
FIG. 4 is a high-level flow diagram illustrating flow rate compensation processing in accordance with an embodiment of the present invention.

FIG. 4 is a high-level flow diagram illustrating flow rate compensation processing in accordance with an embodiment of the present invention. Depending upon the particular implementation, the various process and decision blocks described herein may be performed by hardware components, embodied in machine-executable instructions, which may be used to cause a general-purpose or special-purpose processor or microprocessor programmed with the instructions to perform the steps, or the steps may be performed by a combination of hardware, software, firmware and/or involvement of human participation/interaction.

At block 410, an output signal of a hot-wire anemometer, e.g., an exhalation flow sensor of a medical ventilator, is received. Based on the disclosure provided herein, one of ordinary skill in the art will appreciate a variety of ways in which the output signal of a hot-wire anemometer can be received. For example, the anemometer may be polled or the anemometer may cause a processor to receive an interrupt.

At decision block 420, it is determined whether the hot-wire anemometer is in a transient period. As indicated above, exhalation hot-wire anemometer flow sensors, such as a hot-wire mass flow sensor available from TSI Incorporated of Shoreview, Minn. having part number 840005, Rev. F, have been observed to exhibit transient thermal response during a change in mixture of breathing gas for a period of approximately 30 to 60 seconds. In one embodiment, a time at which a new FiO2 setting is received from a clinician is stored and the determination can be made with respect to elapsed time from receipt of the last setting change. If the hot-wire anemometer is within its transient period, then flow rate compensation processing continues with block 440; otherwise processing branches to block 420.

At block 440, a mix transition factor is determined. The goal of the mix transition factor is to correct for the transient behavior exhibited by the flow sensor at issue and to adjust the output of the flow sensor or a value based thereon so as to increase the accuracy of such values. Based on the disclosure provided herein, one of ordinary skill in the art will appreciate a variety of ways of obtaining and implementing a mix transition factor are available. For example, as indicated above, the corrective modification may be a multiplier involving a constant and an exponentially decaying factor.

At block 450, the mix transition factor determined in block 440 is applied to the output signal or a value based thereon to compensate for the observed transient thermal response of the hot-wire anemometer.

At block 430, the output signal and values based thereon are not corrected. Effectively, no compensation is applied. For example, the mix transition factor (e.g., mix transition multiplier, M of EQ #1) may be designed in such a manner to have no or negligible corrective effect outside of the transient period for the hot-wire anemometer at issue. Alternatively, the mix transition factor may be conditionally applied to the output signal or a value based thereon only during the transient period.

Following block 430 or block 450 flow rate compensation processing is complete.

Figure 5:
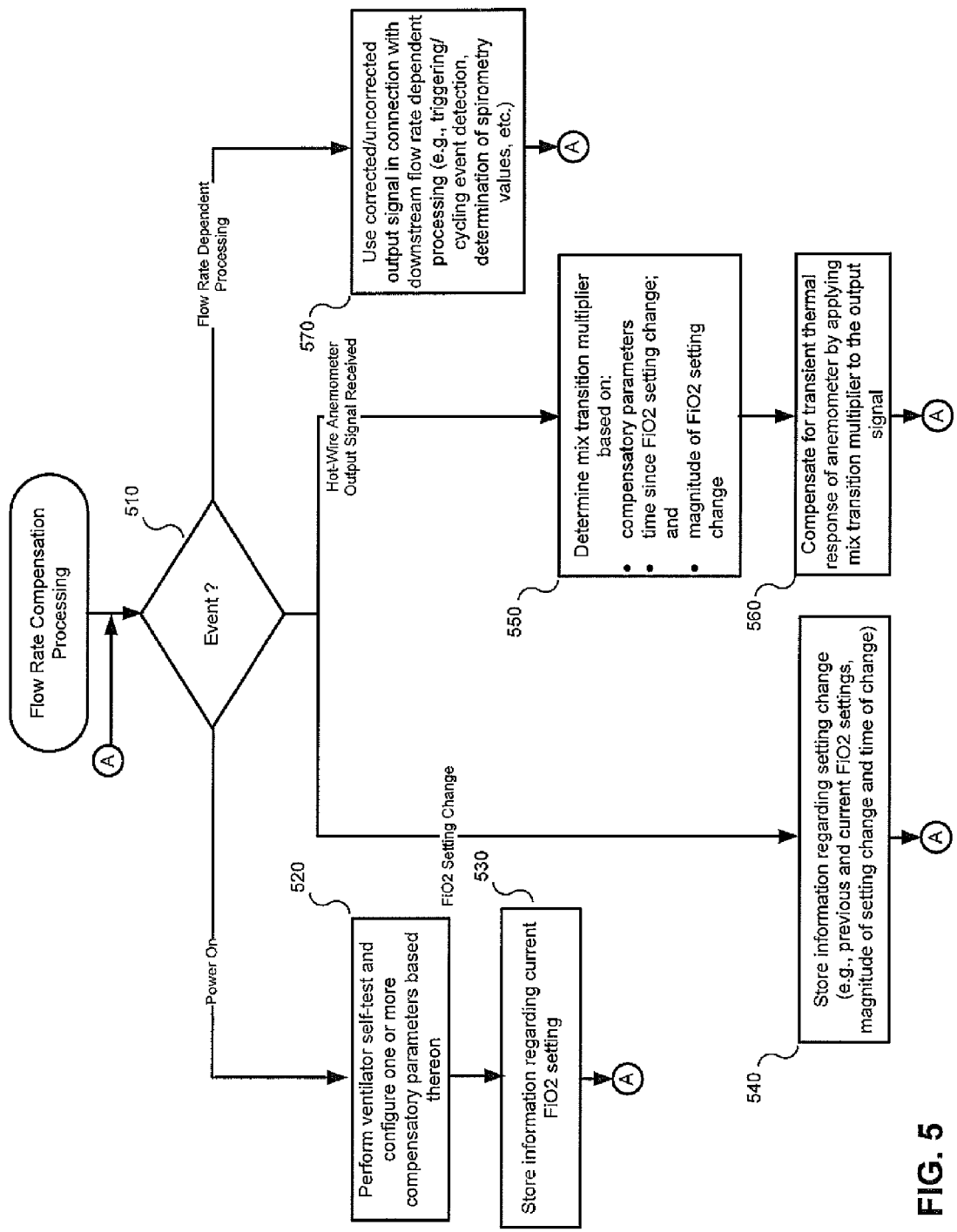
FIG. 5 is a flow diagram illustrating flow rate compensation processing in the context of a medical ventilator in accordance with an embodiment of the present invention.

FIG. 5 is a flow diagram illustrating flow rate compensation processing in the context of a medical ventilator in accordance with an embodiment of the present invention. As indicated above, depending upon the particular implementation, the various process and decision blocks described herein may be performed by hardware components, embodied in machine-executable instructions or the steps may be performed by a combination of hardware, software, firmware and/or involvement of human participation/interaction. In the present example, one or more of the process and decision blocks may be performed by one or more flow sensor processing modules, e.g., flow sensor interface module 321 and/or flow rate compensation module 322.

At decision block 510, an event that trigged the flow rate compensation processing is determined. If the event is a power on event (e.g., a hard or soft reset of the medical ventilator), then processing continues with block 520. If the event is determined to be an FiO2 setting change (e.g., entry by a clinician of a new desired FiO2 setting via a user interface of the medical ventilator), then processing continues with block 540. If the event triggering the flow rate compensation processing is indicative of receipt of an output signal from a hot-wire anemometer (e.g., an exhalation flow sensor of the medical ventilator), then processing continues with block 550. If the event is downstream flow rate dependent processing (e.g., triggering/cycling event detection, determination of spirometry values, etc.) that makes use of the output signal, then processing continues with block 570.

At block 520, ventilator self-test processing is performed during which, among other things, information regarding the current configuration of the medical ventilator is determined. For example, during self-test processing the information regarding the presence and type of flow sensors and current FiO2 setting may be obtained. Based on the flow sensor information, compensatory parameters (e.g., K and T of EQ #1) associated with a mix transition multiplier (e.g., M of EQ #1) may be established for future flow rate compensation processing.

At block 530, information regarding the current FiO2 setting is stored. According to one embodiment, the mix transition multiplier is based at least in part on the magnitude of FiO2 setting changes.

At block 540, a new FiO2 setting has been received. Responsive thereto, information regarding the setting change is stored. In one embodiment, information regarding the previous and current FiO2 settings (e.g., values in the range of 21 to 100, inclusive) are stored as well as the time of the setting change and the magnitude of the setting change.

At block 550, responsive to receipt of an output signal from a hot-wire anemometer, an appropriate mix transition multiplier is determined. In the present example, the mix transition multiplier is M of EQ #1 and is based on the compensatory parameters (i.e., K and T), the time elapsed since the FiO2 setting change and the magnitude of the setting change (i.e., the current FiO2 setting minus the previous FiO2 setting).

At block 560, the mix transition multiplier is applied to the output signal to compensate for the observed transient thermal response of the hot-wire anemometer.

At block 570, during downstream flow rate dependent processing, such as determining an exhaled tidal volume and transitioning a ventilatory cycle of the medical ventilator from an expiratory phase to an inspiratory phase based, the corrected or uncorrected output signal resulting from application of the mix transition multiplier is used.

After completion of blocks 530, 540, 560 or 570, processing branches back to decision block 510 until the next event requiring flow rate compensation processing arises.

In conclusion, embodiments of the present invention provide novel systems, methods and devices for improving spirometry accuracy as well as synchrony between patients and ventilators by employing a computationally efficient model-based approach to enhance measurement accuracy of flow rates and volumes using hot-wire anemometry technology. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method comprising:

one or more flow sensor processing modules of a medical ventilator receiving an output signal of an exhalation flow sensor including a hot-wire anemometer, the output signal indicative of a rate of flow of expired gas by a patient;

the one or more flow sensor processing modules compensating for transient thermal response of the hot-wire anemometer resulting from a change in concentration of gas types included within the expired gas by applying a corrective modification to the output signal or a value based thereon that is based at least in part on a fraction of inspired oxygen (FiO2) being supplied to the patient by the medical ventilator;

wherein the one or more flow sensor processing modules are implemented in one or more microprocessors and one or more computer-readable media, the one or more computer-readable media having instructions tangibly embodied therein that are executable by the one or more microprocessors;

wherein the corrective modification involves a constant and an exponentially decaying factor; and wherein the corrective modification comprises multiplying the output signal or the value based thereon by a mix transition multiplier generally represented as:

$$M = 1.0 + K^* \Delta O2Conc^* e^{-t/T}$$

where, $K = 0.00125$ $T = 15$ seconds $t =$ time elapsed since FiO2 setting change $\Delta O2Conc =$ Current FiO2 setting−Previous FiO2 setting.

2. A medical ventilator comprising:
a breathing gas delivery system having an inspiratory port through which breathing gas is delivered to a patient and an expiratory port through which expired gas is received from the patient;
a flow sensor, including a hot-wire anemometer, operable to measure a rate of flow of expired gas;
a controller coupled to the breathing gas delivery system and the flow sensor, wherein the controller is operable to receive an output signal from the flow sensor indicative of the rate of flow of the expired gas and responsive to receipt of the output signal the controller is further operable to compensate for transient thermal response of the hot-wire anemometer resulting from a change in concentration of gas types included within the expired gas by applying a corrective modification to the output signal or a value based thereon that is based at least in part on a fraction of inspired oxygen (FiO2) being supplied to the patient by the breathing gas delivery system;
wherein the corrective modification involves a constant and an exponentially decaying factor; and
wherein the corrective modification comprises multiplying the output signal or the value based thereon by a mix transition multiplier generally represented as:

$$M = 1.0 + K * \Delta O2Conc * e^{-t/T}$$

where,
K=0.00125
T=15 seconds
t=time elapsed since FiO2 setting change
ΔO2Conc=Current FiO2 setting−Previous FiO2 setting.

3. A program storage device readable by one or more microprocessors of a medical ventilator, tangibly embodying a program of instructions executable by the one or more microprocessors to perform method steps for compensating for transient thermal response of a hot-wire anemometer resulting from a change in concentration of gas types being measured, said method steps comprising:
receiving an output signal of a flow sensor including a hot-wire anemometer that is associated with an expiratory port of the medical ventilator, the output signal indicative of a rate of flow of expired gas by a patient;
compensating for transient thermal response of the hot-wire anemometer resulting from a change in concentration of gas types included within the expired gas by applying a corrective modification to the output signal or a value based thereon that is based at least in part on a fraction of inspired oxygen (FiO2) being supplied to the patient by the medical ventilator; and
wherein the corrective modification comprises multiplying the output signal or the value based thereon by a mix transition multiplier generally represented as:

$$M = 1.0 + K * \Delta O2Conc * e^{-t/T}$$

where,
K=0.00125
T=15 seconds
t=time elapsed since FiO2 setting change
ΔO2Conc=Current FiO2 setting−Previous FiO2 setting.

* * * * *